United States Patent [19]

Bayer

[11] 4,169,092
[45] Sep. 25, 1979

[54] TRANSITION METAL-NAPHTHYRIDINE CHEMICAL COMPLEXES

[76] Inventor: John W. Bayer, R.R. No. 2, Perrysburg, Ohio 43551

[21] Appl. No.: 291,484

[22] Filed: Sep. 22, 1972

Related U.S. Application Data

[63] Continuation of Ser. No. 708,791, Feb. 28, 1968, abandoned.

[51] Int. Cl.$^2$ .................. C09B 69/00; C07F 15/02
[52] U.S. Cl. ........................... 546/10; 106/288 Q; 546/122; 526/141; 526/172; 526/154
[58] Field of Search ........... 260/270 R, 296 N, 270 D

[56] References Cited

U.S. PATENT DOCUMENTS

| | | | |
|---|---|---|---|
| 3,164,599 | 1/1965 | Rapoport | 260/270 R |
| 3,682,594 | 8/1972 | Fish | 260/270 D |
| 3,842,087 | 10/1974 | Williams | 260/296 N |
| 3,843,663 | 10/1974 | Williams | 260/296 N |

OTHER PUBLICATIONS

Bayer, M. S. Thesis, University of Toledo, 1966, pp. 33–40, 48–51, 58–59.
Nebergall, "College Chemistry", Heath, 1957, p. 295.

*Primary Examiner*—Donald G. Daus
*Attorney, Agent, or Firm*—Beveridge, DeGrandi, Kline & Lunsford

[57] ABSTRACT

New coordination complex compounds formed between first row transition metal salts and naphthyridine compounds substituted with electron donor groups at positions ortho and para to the nitrogen positions.

21 Claims, No Drawings

TRANSITION METAL-NAPHTHYRIDINE CHEMICAL COMPLEXES

This is a continuation of application Ser. No. 708,791, filed Feb. 28, 1968, now abandoned.

This invention pertains to new coordination compounds. More particularly, this invention relates to a series of new coordination compounds of the transition metals of certain substituted naphthyridine compounds.

According to the present invention certain transition metal salts are reacted with substituted 1,8-naphthyridines to produce new coordination complex compounds.

The new compounds of this invention are coordination compounds of salts of certain transition metals, and a ligand which is a substituted 1,8-naphthyridine. The chemical combination of the metal ion (the acceptor) with an electron donor (ligand) results in a coordination complex. The complex may be a neutral compound or a charged species, in which case one or more anions of the salt forms an ionic bond with the coordination complex species. When the electron donating species has two or more electron donor groups so that one or more ring structures are formed, the resulting structure is sometimes said to be a "chelate compound" or more simply, a "chelate".

In the present coordination compounds at least one coordinate bond is present wherein a transition metal ion (the acceptor) accepts a share in a pair of electrons furnished by a nitrogen atom in the substituted naphthyridine compound (the donor or ligand). Other coordinate bonds may also be present involving the transition metal ions; for instance, chlorine may also be a donor to the metal ion in forming another coordinate bond.

The substituted naphthyridine used in the present method is one of the family of compounds formed by replacing hydrogen atoms in the naphthyridine ring structure with electron donor groups at one or more positions ortho and para to the nitrogen position.

More specifically, this family of compounds can be structurally defined in terms of 1,8-naphthyridine,

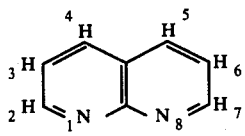

As can be seen, 1,8-naphthyridine is the first of a series of fused ring nitrogen compounds analogous to naphthalene in the fused ring series of aromatic hydrocarbons.

The bonding of a ligand to a metal ion can be quite complex depending upon the coordination number of the metal, the stereochemistry, the structure of the ligand, and the nature of the donor atom. The coordinate bond can be considered as consisting of an electron pair as in covalent bonding but with the electron pair being donated by one atom. Ions of the transition metals have a greater tendency toward coordination than other metal ions, with complexes of these ions being more stable than those formed by electrostatic forces. This may be due to the smaller cation radii of the transition metals compared to those nearer rare gas configuration, thus exhibiting high nuclear or ionic charges.

The transition metals with the exception of copper and zinc, all have incomplete 3d electron orbitals. Consequently, upon reaction, ions of these metals will have a tendency to fill these incomplete orbitals and attain the inert gas structure within spacial limitations. The tendency to assume the inert gas structure is significant but not always attainable. The central metal ion also tends to accept only enough electrons to assume a symmetrical structure of molecules around itself as a central ion. These resulting structures can be planar, tetrahedral, or octahedral, or a distorted structure of each.

THE LIGAND

In general, any ion or molecule having in its structure an atom with an unshared pair of electrons can act as a ligand or coordinating agent. The reactive ligands employed in forming the coordination complexes of the present invention are formed by substituting electron donating groups for the hydrogen atoms at position ortho and para to the naphthyridine nitrogen positions. Referring to the above structure, the ortho and para positions are 2, 4, 5 and 7 while the meta positions are 3 and 6.

Particularly applicable electro-negative groups are lower alkyl, lower alkoxy, (i.e. alkyls and alkoxys having from 1 to 8 carbon atoms), amino and hydroxyl.

Specific examples of suitable substituted naphthyridine compounds which can be used as ligands in forming the transition metal complexes are: 2-methyl-7-hydroxy-1,8-naphthyridine; 2-methyl-5-amino-1,8-naphthyridine; 2-methyl-5,7-dihydroxy-1,8-naphthyridine; 2-amino-5,7-dihydroxy-1,8-naphthyridine; 2-methyl-7-amino-1,8-naphthyridine; 2,4-dihydroxy-1,8-naphthyridine and 7-amino-4-hydroxy-1,8-naphthyridine. Especially useful substituted naphthyridines are 2-methyl-5-hydroxy-1,8-naphthyridine; 2,4-dimethyl-7-amino-1,8-naphthyridine; and 2-hydroxy-4-methyl-7-amino-1,8-naphthyridine.

The mechanics of the ligand coordination reaction are discussed below in terms of 2-methyl-5-hydroxy-1,8-naphthyridine as a ligand. This ligand can be represented by the formula:

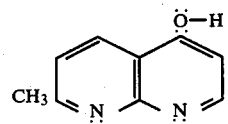

This ligand has 3 positions capable of coordinating. It is known that the oxygen atoms contained in phenolic groups do not form stable coordination compounds. The hydroxyl group associated with the naphthyridine ligand is of a phenolic nature and therefore does not coordinate readily. As will be shown in the examples, the infrared spectra supports this conclusion since the hydroxyl absorption band is the same in the IR spectra for both the ligand and the ligand:transition metal complexes. If coordination had occurred about the hydroxyl oxygen, the hydroxyl absorption band would have been changed.

THE TRANSITION METAL

As used herein the term "first row transition metals" refers to those elements of the periodic table having atomic numbers ranging from 21 to 30. These transition metals are scandium, titanium, vanadium, chromium, manganese, iron, cobalt, nickel, copper and zinc.

Compounds of the foregoing transition metals are used in the method of the invention. In general, such compounds are salts of the transition metals, both organic and inorganic.

Inorganic transition metal salts are especially effective for the purposes of the present invention. These include stronger mineral acid salts such as the halides, nitrates, nitrites, sulfates, and chlorates, of which the halides, sulfates and nitrates are especially noteworthy. Organic salts, such as the transition metal salts of organic acids, for example formates, acetates, propionates, citrates, tartrates, etc., are also applicable.

Specific examples include $Co(NO_3)_2$, $TiCl_4$, $VCl_3$, $VOI_3$, $VOCl_3$, $CrCl_3$, $CrO_2Cl_2$, $MnBr_2$, $FeCl_2$, $Fe(NO_3)_2$, $CoCl_2$, $NiBr_2$, $CuI_2$, $CuCl_2$, $ZnI_2$, $ZnCl_2$, $FeSO_4$, $Co(NO_3)_2$, $NiSO_4$, $Cu_2Cl_2$, $Sc(NO_3)_3$, $ScCl_3$, $FeCl_3$, $VCl_4$, cobaltous acetate, cupric tartrate, nickelous oxalate, zinc-1-phenol-4-sulfonate and nickel benzenesulfonate.

THE LIGAND-TRANSITION METAL COMPLEX

The coordination bonds formed between the substituted naphthyridine and the transition metal forms at either nitrogen atom or both as represented in the structural formula below. In this structural formula the ligand is the quantity enclosed by parenthesis:

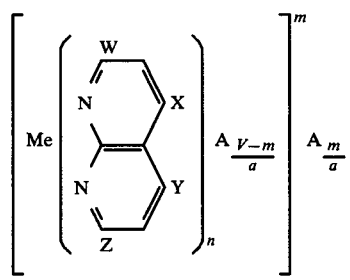

wherein
Me is a transition metal having an atomic number of 21-30;
W, X, Y and Z are groups selected from H and electron donating groups lower alkyl, lower alkoxy, (i.e. alkyls and alkoxys having from 1-8 carbon atoms), —OH and —$NH_2$, wherein no more than three, usually no more than two, H groups are selected;
n is an integer 1, 2 or 3;
A is an anion of an acid;
V is the primary valence of Me;
m is the charge of the coordinated species;
a is the valence of the Anion A;
Me is coordinately bonded with each substituted 1,8-naphthyridine moiety shown in the structural formula solely through one or both ring nitrogen atoms thereof; and when only one such nitrogen atom of each such 1,8-naphthyridine moiety is bonded to Me, n is 2; and
each A within the brackets is coordinately bonded with Me.

In the above structural representation A is an anion of an organic or inorganic acid, usually an anion of a strong mineral acid, especially halide, sulfate and nitrate.

In the above structural representation of the compounds of the present invention, it is seen that the anion (anion from the transition metal salt) can satisfy both the primary valence and the coordination member of the central metal ion. The extent to which the anion is involved in coordination is determined by measuring the conductivity of a solution of the compound. Since conductance is dependent upon the number, size, configuration and space distribution of the ions, the number of conducting species can be determined.

In the present compounds, the primary valences of the central transition metal ions are satisfied by negative ions while the coordination number can be satisfied by either negative ions or neutral ligands. The anion therefore can satisfy both the primary valence and the coordination number and as more anions become coordinated, the number of ions in solution decreases, and the equivalent conductance decreases accordingly.

The general procedure for the synthesis of the naphthyridine complexes comprises dissolving the transition metal compound and the substituted 1,8-naphthyridine in a mutual non-aqueous solvent, e.g., a lower alkanol such as ethanol, heating the reaction mixture, often conveniently by refluxing, and then cooling to effect precipitation of the complex. The precipitates are filtered, washed and dried.

The methods for preparing substituted naphthyridine compounds are known in the art. For instance, see Allen, C.F.H., Chem. Rev. 47, 2754 (1950) and references cited; Brown, E. V., J. Org. Chem., 30, No. 5, 1607+(1965); Lappin, G. R., J. Am. Chem. Soc., 70, 3348 (1948). The method employed in the following examples employs the cyclization of substituted 2-amino pyridines.

Preparation of Transition Metal Complexes of 2-methyl-5-hydroxy-1,8 naphthyridine

EXAMPLE I

A. Preparation of the Ligand

Step 1. Preparation of ethyl-6-methyl-2-pyridylaminomethylenemalonate

Reaction

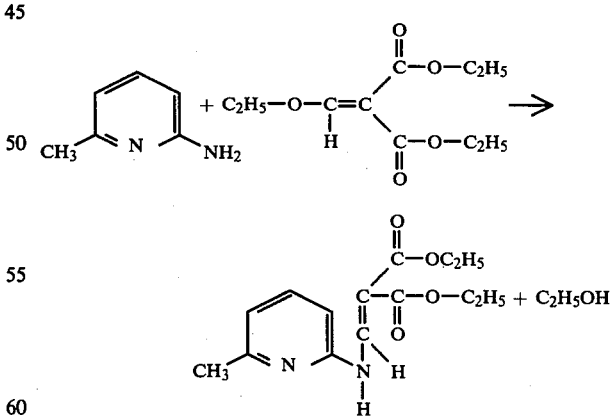

Procedure

Diethylethoxymethylenemalonate (250 g.) and 6-methyl-2-aminopyridine (130 g.) were heated together in a one liter three-neck flask fitted with a mechanical stirrer, a fractionating condenser, and a thermometer. Reflux was maintained for one-half hour, and the ethanol distilled at a rate to maintain a pot temperature of 110° C. After reaction time, the mixture was poured into a one-liter beaker and allowed to cool. The pale yellow solid was broken up and dissolved in 600 ml. of refluxing ethanol. Upon cooling, the mixture was filtered, dried, and the precipitate recrystallized a second time from 600 ml. ethanol. The yellow solid was again filtered and the precipitate dried under vacuum at 45° C. for eight hours. The resulting 265.3 g. of light yellow crystals melt at 103°–104° C. This represents 86.5% yield of theoretical. Theoretical melting point of ethyl-6-methyl-2-pyridylaminomethylenemalonate is 103°–104° C.

Step 2. Preparation of the ethyl ester of 2-methyl-5-hydroxy-1,8-naphthyridine-6-carboxylic acid Equation

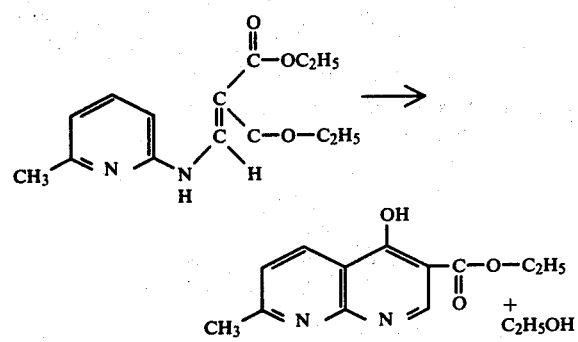

Procedure

To a one-liter flask were added 75 g. of the pyridylmalonate prepared above, and 450 ml. of diphenyl ether. The flask was fitted with a mechanical stirrer, a thermometer, and a fractionating condenser. The reaction mixture was heated to reflux for 45 minutes with distillation maintained at a rate to keep the pot temperature at approximately 200° C. After reflux, the mixture was cooled to room temperature and mixed with 900 ml. of hexane. The dark brown precipitate was filtered, washed with hexane, and dried under vacuum for 24 hours at 90° C. The procedure was repeated three additional times using the remaining pyridylmalonate. In all, 183.5 g. of brown solid having a melting point at 258°–260° C. (theoretical 258°–261° C.) was obtained. This represents a yield of 82% theoretical.

Step 3. Preparation of 2-methyl-5-hydroxy-1,8-naphthyridine-6-carboxylic acid

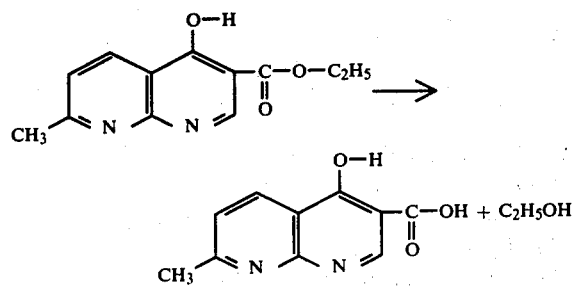

Procedure

To a one liter flask were added 750 ml. of 10% NaOH aqueous solution and 60 g. of ethyl ester prepared in step 2 above. The flask was fitted with a mechanical stirrer and a fractionating condenser. The mixture was heated to reflux for two hours, distilling off the alcohol formed. After two hours, the reaction mixture was filtered while hot to remove any unreacted ester. The filtrate was cooled and made just acid to pH paper with concentrated hydrochloric acid. The resulting light brown precipitate was filtered off, washed with water, and vacuum dried at 90° C. The procedure was repeated twice in order to use the remaining ester. In all, 147.7 g. of light brown solid results, melting at 278°–280° C. (theoretical 278°–280° C.). This represents a yield of 92.5% theoretical.

Step 4. Preparation of 2-methyl-5-hydroxy-1,8-naphthyridine

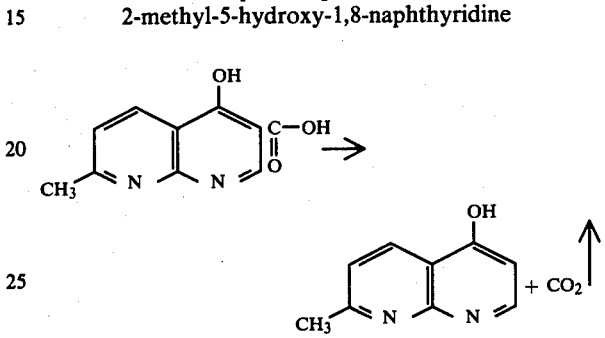

Procedure

Twenty grams of the acid prepared in section 3 above were added over a period of ten minutes to 300 ml. of heavy mineral oil maintained at 300° C. in a 600 ml. beaker equipped with a magnetic stirrer. After the ten minutes, the mineral oil solution was decanted from the black tarry residue into a one-liter beaker. Crystallization occurred upon cooling. After cooling to room temperature, 600 ml. of hexane was added. The precipitate was filtered, washed thoroughly with hexane and dried by passing air through the filter. The light tan precipitate was recrystallized from 200 ml. of boiling water. The procedure was repeated six additional times to use the remaining naphthyridine acid. Upon vacuum drying at 90° C., 56 g of tan platelets result, melting at 236°–237° C. (theoretical 238°–240° C.) This yield represents 69.5% of theoretical.

The elemental analysis of 2-methyl-5-hydroxy-1,8-naphthyridine is as follows:

|  | Actual | Theoretical |
|---|---|---|
| Carbon | 66.53 | 67.5 |
| Hydrogen | 5.03 | 5.01 |
| Nitrogen | 17.09 | 17.5 |

B. Preparation of metal Complexes of 2-methyl-5-hydroxy-1,8-naphthyridine

EXAMPLE 2

1. Preparation of the chromium (III) complex of 2-methyl-5-hydroxy-1,8-naphthyridine To 65 ml. of refluxing 95% ethanol were added 4.8 g. (0.03 m.) of 2-methyl-5-hydroxy-1,8-naphthyridine and 2.66 g. (0.01 m.) $CrCl_3 \cdot 6H_2O$. Refluxing was continued until solution was complete and the mixture then cooled to about 0° C. Precipitation started on about the sixth day and appeared to be complete after two weeks. The green-tan ethanol insoluble solid was filtered off and the precipitate vacuum dried at 60° C. with 1.3 g. resulting. This solid had a melting point of about 200°–205° C. and melting into a dark fluid. The filtrate was then mixed with 200 ml. of dry acetone and the resulting acetone insoluble precipitate filtered. Upon vacuum drying at 60° C., 2.0 g. of olive-green solid remains. This solid had a melting point of about 325° C. and melted into a dark fluid.

The recovered complexes (ethanol insoluble and acetone insoluble) were analyzed for carbon, hydrogen, nitrogen and chlorine. The carbon, hydrogen and nitrogen analyses were performed using a F and M Scientific Company analyzer wherein the sample is oxidized in a stream of argon and the gases passed through a gas chromatograph. Carbon is analyzed as $CO_2$, hydrogen as water, and the nitrous oxides reduced and analyzed as $N_2$. Chlorine was analyzed by the Volhard method, wherein the sample is refluxed in an aqueous KOH solution for 2 hours, titrated with excess $AgNO_3$, and the excess silver back titrated with ammonium thiocyanate. (See Kolthoff, I. M. and Stenger V. A.) "Volumetric analysis," Vol. II, Interscience Publishers, New York (1947) p. 261. As expected, chlorine analyses gave low values.

|  | Actual Analysis | | | |
|---|---|---|---|---|
| Actual Compound | % C | % H | % N | % Cl |
| $Cr^{+3}$ complex(ethanol insoluble) | 41.8 | 4.84 | 10.18 | 12.1 |
| $Cr^{+3}$ complex(acetone insoluble) | 55.3 | 5.32 | 13.67 | 9.62 |

|  | Theoretical Analysis | | | |
|---|---|---|---|---|
| Theoretical Compound | % C | % H | % N | % Cl |
| $CrCl_3 \cdot 2C_9H_8N_2O$ | 45.2 | 3.36 | 11.7 | 22.2 |
| $CrCl_3 \cdot 3C_9H_8N_2O$ | 55.1 | 4.09 | 14.3 | 18.1 |

From the above it is seen that the acetone insoluble compound has a 3:1 ligand to metal ratio and has the structure formula

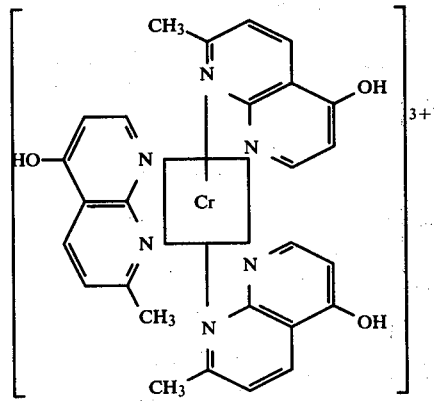

This compound is named tris(2-methyl-5-hydroxy-1,8-naphthyridine) chromium (III) chloride according to IUPAC nomenclature.

The ethanol insoluble compound has a 2:1 ligand to metal ratio and has the structural formula:

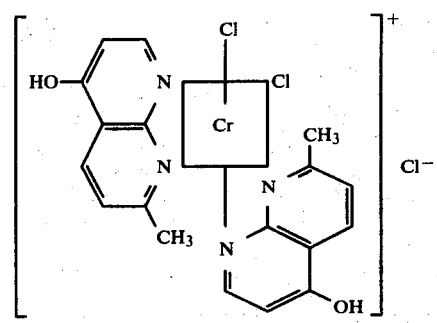

The IUPAC name for this compound is dichlorobis(2-methyl-5-hydroxy-1,8-naphthyridine) chromium (III) chloride.

Similarly, when 0.01 mole of scandium trichloride is substituted for the chromium trichloride in the foregoing procedure, the main product is the ethanol insoluble dichlorobis(2-methyl-5-hydroxy-1,8 naphthyridine) scandium (III) chloride.

EXAMPLE 3

2. Preparation of the iron (II) complex of 2-methyl-5-hydroxy-1,8-naphthyridine

To 65 ml. of refluxing 95% ethanol were added 4.8 g. (0.03 m.) of 2-methyl-5-hydroxy-1,8-naphthyridine and 1.98 g. (0.01 m.) of $FeCl_2 \cdot 4H_2O$ with refluxing continued until solution was complete. Upon cooling a fine, red-brown precipitate formed. This was set aside in a refrigerator for one week. The precipitate was filtered off and vacuum dried at 60° C. Four grams of red-brown solid results. This solid has a melting point of 155°–160° C. and melted into a dark tarry mass. The filtrate was added to acetone but no further precipitation occurred.

The reaction product was analyzed according to the method of Example 2. The results are set forth below.

|  | Actual Composition | | | |
|---|---|---|---|---|
|  | % C | % H | % N | % Cl |
|  | 45.1 | 4.39 | 10.74 | 13.0 |

|  | Theoretical Composition | | | |
|---|---|---|---|---|
| Theoretical Compound | % C | % H | % N | % Cl |
| $FeCl_2 \cdot C_9H_8N_2O$ | 41.2 | 2.79 | 9.8 | 24.8 |
| $FeCl_2 \cdot 2C_9H_8N_2O$ | 48.5 | 3.59 | 12.6 | 15.9 |

The elemental analysis indicates that the structure is between a 1:1 and a 2:1 ligand:metal ratio which indicates that a mixture of the two complexes is present. The infrared spectra leaves no doubt that the nitrogen is the electron donating atom. The structure was determined to be that of tetrahedal configuration as indicated by the high extinction coefficient of the visible spectra.

The reaction product isolated is then a mixture of two complexes, one of which is:

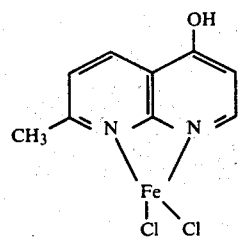

The IUPAC name for this compound is Dichloro(2-methyl-5-hydroxy-1,8-naphthyridine)iron (II).

The other complex is:

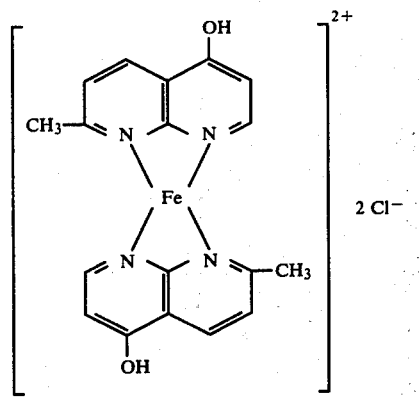

The IUPAC name for this compound is Bis(2-methyl-5-hydroxy-1,8-naphthyridine)iron (II) chloride.

EXAMPLE 4

3. Preparation of the cobalt (II) complex of 2-methyl-5-hydroxy-1,8-naphthyridine To 65 ml. of refluxing 95% ethanol were added 4.8 g. (0.03 m.) of 2-methyl-5-hydroxy-1,8-naphthyridine and 2.37 g. (0.01 m.) of $CoCl_2.6H_2O$. Refluxing was continued until solution was complete. The mixture was set aside in a refrigerator for one week, with precipitation occurring on the third day. The mixture was filtered and the precipitate vacuum dried with 4.2 g. of deep blue solid resulting. This solid had a melting point of 250°–252° C. and melted into a dark tarry mass. The filtrate was added to 200 ml. of acetone with no precipitation.

The reaction product was analyzed according to the method of Example 2, and the results are set forth below:

| | Actual Composition | | |
|---|---|---|---|
| % C | % H | % N | % Cl |
| 40.6 | 3.89 | 1.66 | 14.0 |

| Theoretical Compound | Theoretical Composition | | | |
|---|---|---|---|---|
| $CoCl_2 . C_9H_8N_2O$ | 37.4% C | 2.77% H | 9.67% N | 24.2% Cl |
| $CoCl_2 . 2C_9H_8N_2O$ | 48.2% C | 3.58% H | 12.5% N | 15.8% Cl |

The elemental analysis indicates that the structure is between a 1:1 and a 2:1 ligand-metal ratio which indicates that a mixture of the two complexes is present. The visible spectra has the characteristic absorption and high extinction coefficients that signify the tetrahedral geometric structure. Stoichiometric calculations from the percent carbon indicate that the mixture contains 30% 2:1 ligand:cobalt complex and 70% 1:1 ligand:cobalt complex. The 1:1 ligand:cobalt complex is a non-electrolyte with the chloride ions satisfying the coordination number. The structure is:

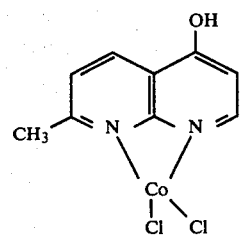

This compound can be expressed more conveniently as:

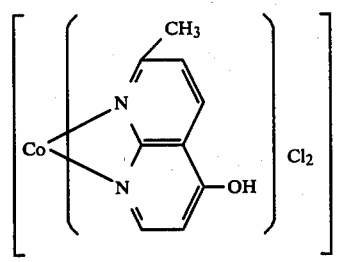

The IUPAC name for this compound is Dichloro-2-methyl-5-hydroxy-1,8-naphthyridine)cobalt (II).

The 2:1 ligand:cobalt complex has the coordination number satisfied by the ligand acting as a bidentate, with the chloride ions satisfying the primary valence of the cobalt. This structure for this compound is:

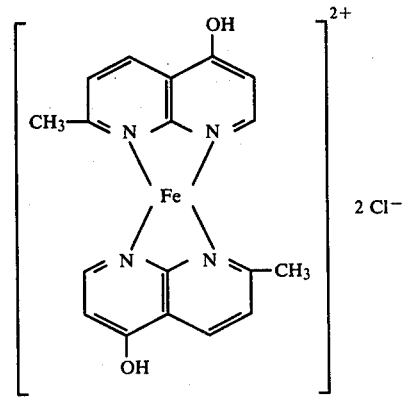

This compound can be expressed more conveniently as

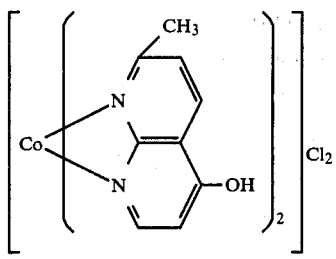

The IUPAC name for this compound is Bis(2-methyl-5-hydroxy-1,8-naphthyridine)cobalt (II) chloride.

EXAMPLE 5

4. Preparation of the nickel (II) complex of 2-methyl-5-hydroxy-1,8-naphthyridine To 65 ml. of refluxing 95% ethanol were added 4.8 g. (0.03 m.) of 2-methyl-5-hydroxy-1,8-naphthyridine and 2.37 g. (0.01 m.) of $NiCl_2.6H_2O$. Refluxing was continued until solution occurred. The solution was set aside in a refrigerator for one week, with precipitation occurring on the second day. The mixture was filtered and the precipitate vacuum dried at 60° C., 4.7 g. of yellow-tan solid resulting. This solid has a melting point of 215°–218° C. and melted into a dark viscous mass. No further precipitation occurred when the filtrate was added to acetone.

The reaction product was analyzed according to the method of Example 2 and the results are set forth below:

| | Actual Composition | | |
|---|---|---|---|
| % C | % H | % N | % Cl |
| 39.0 | 5.24 | 10.07 | 11.8 |

| Theoretical Compound | Theoretical Composition | | | |
|---|---|---|---|---|
| $NiCl_2 . C_9H_8N_2O$ | 37.4% C | 2.77% H | 9.67% N | 24.4% Cl |
| $NiCl_2 . 2C_9H_8N_2O$ | 48.2% C | 3.58% H | 12.5% N | 15.8% Cl |

The elemental analysis indicates that the structure is between a 1:1 and a 2:1 ligand:metal ratio which indicates that a mixture of the two complexes is present. The visible absorption spectra is indicative of square planar structure configuration. Also the extinction coefficients of the absorptions are low as would be expected. The infrared spectra indicates that coordination occurred through the nitrogen. Stoichiometric calculations from the percent carbon indicates that mixture contains 85% 1:1 and 15% 2:1 ligand:nickel complexes.

The structure for the 1:1 ligand:nickel complex is:

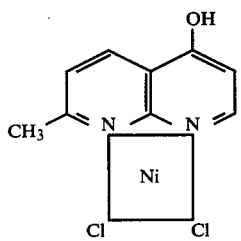

This compound can be expressed more conveniently as

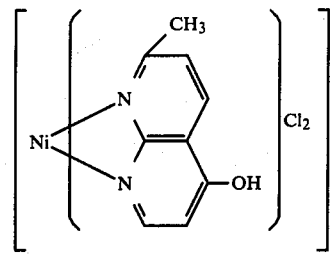

The IUPAC name for this compound is Dichloro(2-methyl-5-hydroxy-1,8-naphthyridine)nickel (II).

The structure for the 2:1 ligand:cobalt complex is:

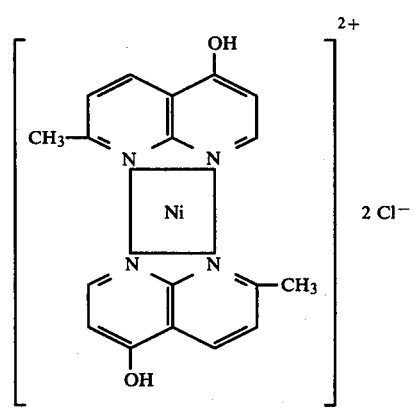

Bis(2-methyl-5-hydroxy-1,8-naphthyridine)nickel (II) chloride.

This compound can be expressed more conveniently as

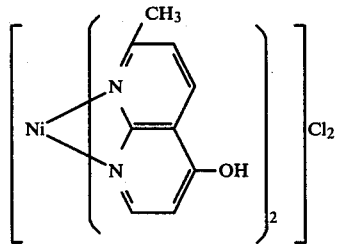

Experimental note on Examples 3, 4 and 5

Since these reaction products appeared to be mixtures of two complexes, the reaction products were recrystallized from 95% ethanol and reanalyzed.

| Examples | % C | % H | % N |
|---|---|---|---|
| 3 | 46.6 | 3.78 | 10.6 |
| 4 | 40.9 | 4.65 | 10.9 |
| 5 | 38.1 | 5.10 | 10.3 |

This analytical data is within the experimental error of the original analysis presented for the compounds in Examples 3, 4 and 5. This indicates that the complexes are not subject to further purification upon recrystallization from ethanol.

EXAMPLE 6

5. Preparation of the copper (II) complex of 2-methyl-5-hydroxy-1,8-naphthyridine To 60 ml. of refluxing 95% ethanol were added 4.8 g. (0.03 m.) of 2-methyl-5-hydroxy-1,8-naphthyridine and heated continually until solution was complete. To another 60 ml. of refluxing ethanol were added 1.70 g. (0.01 m.) of $CuCl_2.2H_2O$ with refluxing continued until solution occurred. The two solutions were then mixed with a bright green precipitate forming immediately. The mixture was cooled and filtered, the precipitate being vacuum dried at 60° C., with 2.0 g. of green solid remaining. The filtrate was heated to reflux and another 1.70 g. of $CuCl_2.2H_2O$ dissolved therein. Precipitation again occurred with 2.7 g. of green precipitate resulting upon work-up as before. To the filtrate of this step, an additional 1.70 g. of $CuCl_2.2H_2O$ was added with 1.9 g. of precipitate remaining. A final similar procedure produced no precipitate. The total yield was 6.6 g. This solid has a melting point of 175°–176° C. and melted into a dark fluid.

The reaction product was analyzed according to the method of Example 2 and the results are set forth below:

|  | Actual Composition | | |
|---|---|---|---|
| % C | % H | % N | % Cl |
| 36.4 | 2.62 | 9.41 | 24.1 |

| Theoretical Compound | Theoretical Composition | | |
|---|---|---|---|
| $CuCl_2.C_9H_8N_2O$ | 36.7%C | 2.72%H | 9.50%N | 24.0%Cl |

The elemental analysis indicates that the structure is 1:1 ligand:metal complex. The visible spectrum agrees with that of known copper complexes having a single broad absorption band. The complex has a high extinction coefficient which is explained by the fact that copper (II) complexes distort toward a tetrahedral structure thus yielding higher extinction coefficients than exhibited by true square planar complexes.

The structure for this complex is

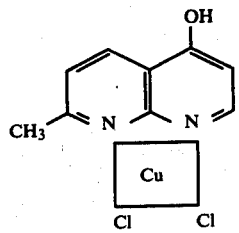

More conveniently expressed, this formula is:

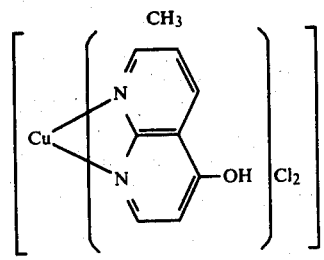

The IUPAC name for this compound is Dichloro(2-methyl-5-hydroxy-1,8-naphthyridine)copper (II).

EXAMPLE 7

6. Preparation of the zinc complex of 2-methyl-5-hydroxy-1,8-naphthyridine

To 65 ml. of refluxing 95% ethanol were added 4.8 g. (0.03 m.) of 2-methyl-5-hydroxy-1,8-naphthyridine and 1.36 g. (0.01 m.) of anhydrous $ZnCl_2$. The resulting solution was set aside in the refrigerator for one week with precipitation occurring on the second day. The precipitate was filtered with 5.1 g. of tan precipitate resulting upon vacuum drying at 60° C. This solid has a melting point of 224°–228° C. and melted into a colorless fluid. No precipitate resulted upon adding the filtrate to 200 ml. of acetone.

The reaction product was analyzed according to the method of Example 2 and the results are set forth below:

|  | Actual Composition | | |
|---|---|---|---|
| % C | % H | % N | % Cl |
| 47.5 | 3.78 | 12.45 | 12.2 |

| Theoretical Compound | Theoretical Composition | | |
|---|---|---|---|
| $ZnCl_2.2C_9H_8N_2O$ | 47.3%C | 3.44%H | 12.3%N | 15.1%Cl |

This elemental analysis confirms the 2:1 ligand:zinc complex. Molar conductance values indicate that the chloride ions are coordinated rather than ionic. The coordination number is then satisfied by the ligand in monodentate structure arrangement.

This structure is represented by:

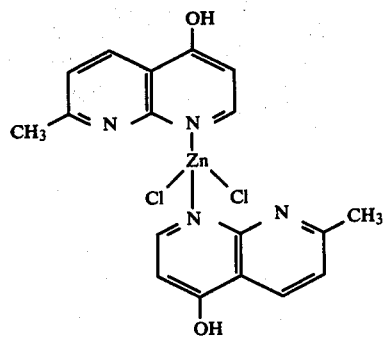

More conveniently this structure is expressed by:

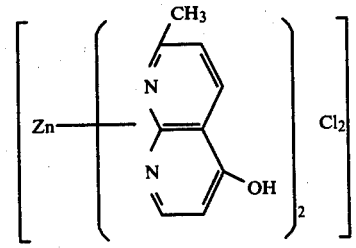

The IUPAC name for this complex is Dichlorobis(2-methyl-5-hydroxy-1,8-naphthyridine)zinc (II).

A comparison of the chlorine values indicates that the actual chlorine analyzed is quite low as compared to the theoretical chlorine content. One possible explanation is that there is direct ion coordination between the particular transition metal and the chlorine to satisfy the coordination number of the metal. This would account for the low chlorine value since the chlorine complexed in this manner would not readily hydrolyze in the KOH analytical solution.

The solubility in common solvents of the compounds prepared in Examples 2-7 is set forth in the following table:

| | Solubilities of the 2-methyl-5-hydroxy-1,8-naphthyridine complexes | | | | | | |
|---|---|---|---|---|---|---|---|
| | Solvent | | | | | | |
| Example | $H_2O$ | Alcohol | Acetone | Nitrobenzene | Acetonitrile | Chloroform | Dimethylformamide |
| ($Cr^{+3}$) | s | s | i | i | i | i | s |
| 3 ($Fe^{+2}$) | s | s | i | i | i | i | s |
| 4 ($Co^{+2}$) | s | s | s.s. | i | s | i | s |
| 5 ($Ni^{+2}$) | s | s | s.s. | i | s | i | s |
| 6 ($Cu^{+2}$) | s | s | i | i | i | i | s |
| 7 ($Zn^{+2}$) | s | s | s.s. | i | s | i | s | s indicates a solubility of $10^{-2}$ M or greater.
s.s indicates a solubility of $10^{-3}$ M, but not soluble at $10^{-2}$ M.
i indicates a solubility of less than $10^{-3}$ M.

EXAMPLE 8

Preparation of $Co(NO_3)_2$ complex of 2-methyl-5-hydroxy-1,8-naphthyridine

To 65 ml. of refluxing 95% ethanol were added 2.91 g. of $Co(NO_3)_2.6H_2O$ and heated until solution was complete. 4.8 g. of 2-methyl-5-hydroxy-1,8-naphthyridine were added to this refluxing solution. Upon reaction 4.0 grams of product was obtained.

The reaction product was analyzed according to the method of Example 2 and the results are set forth below:

| Actual Composition | | |
|---|---|---|
| % C | % H | % N |
| 51.0 | 4.0 | 17.6 |

| Theoretical Compound | Theoretical Composition | | |
|---|---|---|---|
| $Co(NO_3)_2.3C_9H_8N_2O$ | 49.0% C | 3.6% H | 16.9% N |

The structure for this complex can be expressed as:

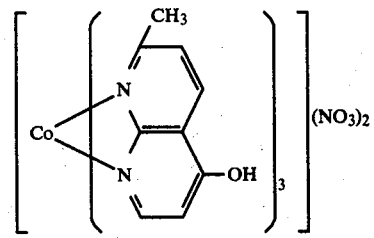

EXAMPLE 9

Preparation of 2,4-dimethyl-7-amino-1,8-naphthyridine

Preparation of the Ligand

Equation

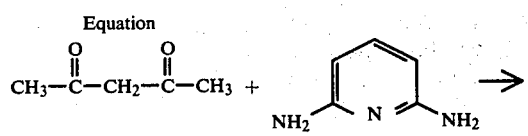

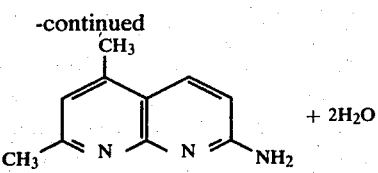

Procedure

Twenty grams of 2,6-diamino pyridine were added to 100 ml. of 85% phosphoric acid ($H_3PO_4$) and 20 ml. of acetylacetone were then added to this mixture in a reaction flask fitted with a mechanical stirrer. A reflux condenser and a thermometer were then installed and the solution was maintained for 30 minutes at approximately 100° C. with stirring and then allowed to cool. The cooled mixture was then poured into 500 ml. of water that had been made basic to pH 11 through the addition of NaOH. The product 2,4-dimethyl-7-amino-1,8-naphthyridine precipitated and was filtered and was recrystallized from water. Eight grams of product was recovered having a melting point of 262°-264° C.

EXAMPLE 10

Preparation of $CoCl_2$ complex of 2,4-dimethyl-7-amino-1,8-naphthyridine

To 65 ml. of refluxing 95% ethanol were added 2.91 grams of $CoCl_2.6H_2O$ and heated until solution was complete. 3.46 g. of 2,4-dimethyl-7-amino-1,8-naphthyridine were added to this refluxing solution. Upon reaction 4.5 grams of product was obtained.

The reaction product was analyzed according to the method of Example 2 and the results are set forth below.

| Actual Composition | | |
|---|---|---|
| % C | % H | % N |
| 50.1 | 5.2 | 16.6 |

| Theoretical Compound | Theoretical Composition | | |
|---|---|---|---|
| $CoCl_2.C_{10}H_{11}N_3$ | 39.6% C | 3.6% H | 13.8% N |
| $CoCl_2.2C_{10}H_{11}N_3$ | 50.3% C | 4.7% H | 17.7% N |

The structure for this information can be expressed as:

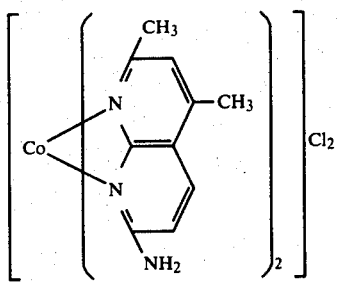

EXAMPLE 11

Preparation of NiCl₂ complex of 2,4-dimethyl-7-amino-1,8-naphthyridine 3.46 grams of 2,4-dimethyl-7-amino-1,8-naphthyridine was added to 65 mls. of refluxing ethanol with stirring until solution was complete. 2.38 gms. of $NiCl_2 \cdot 6H_2O$ was then added and the solution was refluxed for about 15 minutes. The mixture was then cooled and the resulting precipitate was filtered with ethanol and dried in a vacuum oven. 3.9 grams of product were obtained.

The reaction product was analyzed according to the method of Example 2 and the results are set forth below:

|  | Actual Composition | |
| --- | --- | --- |
| % C | % H | % N |
| 50.1 | 5.1 | 17.6 |

| Theoretical Compound | Theoretical Composition | | |
| --- | --- | --- | --- |
| $NiCl_2 \cdot C_{10}H_{11}N_3$ | 39.6% C | 3.6% H | 13.8% N |
| $NiCl_2 \cdot 2C_{10}H_{11}N_3$ | 50.3% C | 4.7% H | 17.7% N |

The structure for this information can be expressed as:

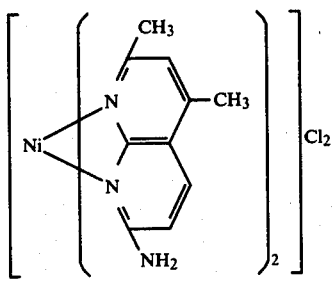

EXAMPLE 12

Preparation of CuCl₂ complex of 2,4-dimethyl-7-amino-1,8-naphthyridine 5.1 grams (0.03 mole) of 2,4-dimethyl-7-amino-1,8-naphthyridine was added to 100 ml. of refluxing ethanol with stirring until solution was complete. 1.7 grams (0.01 m.) of $CuCl_2 \cdot 2H_2O$ was then added and the solution was refluxed for about 15–30 minutes. The mixture was then cooled and the resulting precipitate was filtered with ethanol and dried in a vacuum oven. 4.5 grams of product were obtained.

The reaction product was analyzed according to the procedure of Example 2 and the results are set forth below:

|  | Actual Composition | |
| --- | --- | --- |
| % C | % H | % N |
| 50.5 | 5.1 | 18.0 |

| Theoretical Compound | Theoretical Composition | | |
| --- | --- | --- | --- |
| $CuCl_2 \cdot C_{10}H_{11}N_3$ | 35.0% C | 3.6% H | 13.6% N |
| $CuCl_2 \cdot 2C_{10}H_{11}N_3$ | 49.9% C | 4.6% H | 17.4% N |

The structure for this information can be expressed as:

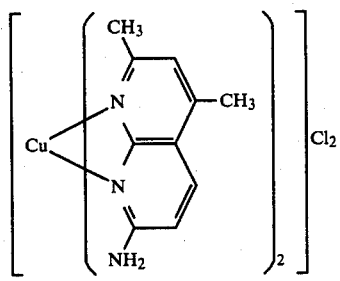

EXAMPLE 13

Preparation of FeCl₂ complex of 2,4-dimethyl-7-amino-1,8-naphthyridine 5.1 gms. (0.03 m.) of 2,4-dimethyl-7-amino-1,8-naphthyridine was added to 100 ml. of refluxing ethanol with stirring until solution was complete. 1.98 gms. (0.01 m.) of $FeCl_2 \cdot 4H_2O$ was then added and the solution was refluxed for about 15–30 minutes. The mixture was then cooled and the resulting precipitate was filtered with ethanol and dried in a vacuum oven. 4.5 grams of product were obtained.

The reaction product was analyzed according to the method of Example 2 and the results are set forth below:

|  | Actual Composition | |
| --- | --- | --- |
| % C | % H | % N |
| 46.0 | 5.3 | 15.7 |

| Theoretical Compound | Theoretical Composition | | |
| --- | --- | --- | --- |
| $FeCl_2 \cdot C_{10}H_{11}N_3$ | 40% C | 3.7% H | 14% N |
| $FeCl_2 \cdot 2C_{10}H_{11}N_3$ | 51% C | 4.7% H | 17.8% N |

The structures for this information can be expressed as:

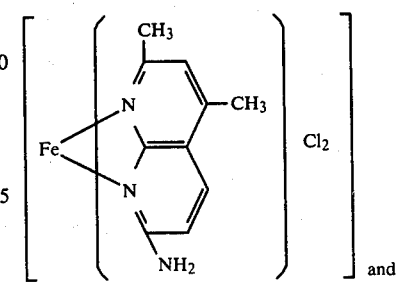

and

-continued

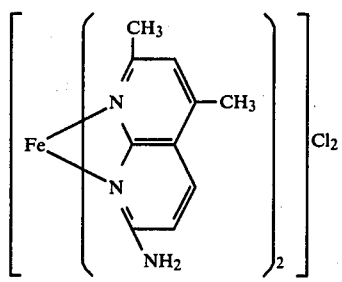

EXAMPLE 14

Preparation of CoBr$_2$ complex of 2,4-dimethyl-7-amino-1,8-naphthyridine 5.1 gms. (0.03 m.) of 2,4-dimethyl-7-amino-1,8-naphthyridine was added to 100 ml. of refluxing ethanol with stirring until solution was complete. 2.37 gms. of CoBr$_2$ was then added and the solution was refluxed for about 15–30 minutes. The mixture was then cooled and the resulting precipitate was filtered with ethanol and dried in a vacuum oven. 5.2 gms. of product were obtained.

The reaction product was analyzed according to the method of Example 2 and the results are set forth below:

| | Actual Composition | |
|---|---|---|
| % C | % H | % N |
| 41.2 | 4.4 | 14.3 |
| Theoretical Compound | Theoretical Composition | |
| CoBr$_2$.C$_{10}$H$_{11}$N$_3$ | 30.6% C  2.8% H | 10.7% N |
| CoBr$_2$.2C$_{10}$H$_{11}$N$_3$ | 42.4% C  3.9% H | 14.9% N |

The structure for this information can be expressed as:

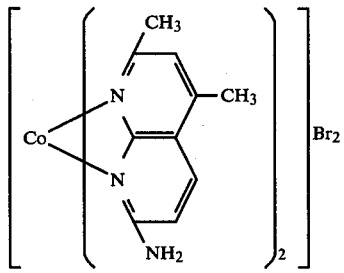

EXAMPLE 15

Preparation of Co(NO$_3$)$_2$ complex of 2,4-dimethyl-7-amino-1,8-naphthyridine 3.5 grams of 2,4-dimethyl-7-amino-1,8-naphthyridine were added to 65 ml. of refluxing ethanol with stirring until solution was complete. 2.9 grams of Co(NO$_3$)$_2$.6-H$_2$O was then added and the solution was refluxed for about 15 minutes. The mixture was then cooled and the resulting precipitate was filtered with ethanol and dried in a vacuum oven. 4.0 grams of product were obtained.

The reaction product was analyzed according to the method of Example 2 and the results are set forth below:

| | Actual Composition | |
|---|---|---|
| % C | % H | % N |
| 41.0% C | 4.8% H | 18.2% N |
| Theoretical Compound | Theoretical Compound | |
| Co(NO$_3$)$_2$.C$_{10}$H$_{11}$N$_3$ | 33.7% C  3.1% H | 19.7% N |
| Co(NO$_3$)$_2$.2C$_{10}$H$_{11}$N$_3$ | 45.5% C  4.2% H | 21.2% N |

The structure for this information can be expressed as:

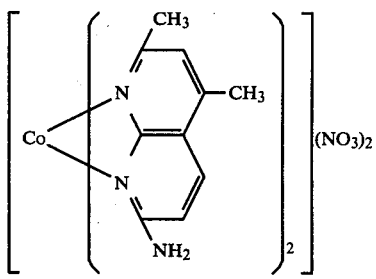

The IUPAC name for this compound is bis(2,4-dimethyl-7-amino-1,8-naphthyridine)cobalt (II) nitrate.

IUPAC names for the coordination compounds of examples 8,10,11,12,13 and 14 are, respectively, tris(2-methyl-5-hydroxy-1,8-naphthyridine)cobalt (II) nitrate; bis(2,4-dimethyl-7-amino-1,8-naphthyridine)cobalt (II) chloride; bis(2,4-dimethyl-7-amino-1,8-naphthyridine)-nickel (II) chloride; bis(2,4-dimethyl-7-amino-1,8-naphthyridine)copper (II) chloride; dichloro(2,4-dimethyl-7-amino-1,8-naphthyridine)iron (II) (first compound) and bis(2,4-dimethyl-7-amino-1,8-naphthyridine)iron (II) chloride (second compound); bis(2,4-dimethyl-7-amino-1,8-naphthyridine)cobalt (II) bromide.

EXAMPLES 16–22

A series of transition metal complexes was prepared by contacting the ligand 2,4-dimethyl-7-amino-1,8-naphthyridine (0.03 mole) and 0.01 mole of the metal salt indicated in the following table in about 100 ml. of refluxing ethanol for 15 minutes, cooling, filtering the precipitated reaction product, washing it with ethanol and thereafter drying the washed product under vacuum at 50° C. The following table indicates the salt used and the product obtained, shown as a simplified formula wherein L represents the ligand 2,4-dimethyl-7-amino-1,8-naphthyridine:

| Example | Salt | Coordination Compound | Grams |
|---|---|---|---|
| 16 | TiCl$_4$ | [Ti(L)$_2$Cl$_2$] Cl$_2$ | 5.9 |
| 17 | VCl$_3$ | [V(L)Cl$_2$] Cl | 4 |
| 18 | VOCl$_3$ | [VO(L)$_3$] Cl$_3$ | 6.1 |
| 19 | CrCl$_3$ | [Cr(L)$_3$]Cl$_3$ | 6 |
| 20 | MnCl$_2$ | [Mn(L)$_2$Cl$_2$] | 5.1 |
| 21 | FeCl$_3$ | [Fe(L)$_2$Cl$_2$] Cl | 5.4 |
| 22 | ZnCl$_2$ | [Zn(L)Cl$_2$] | 5.4 |

-continued

| COORDINATION COMPOUND NAME |
|---|
| 16 dichlorobis(2,4-dimethyl-7-amino-1,8-naphthyridine)titanium(IV) chloride |
| 17 dichloro(2,4-dimethyl-7-amino-1,8-naphthyridine)vanadium(III) chloride |
| 18 tris(2,4-dimethyl-7-amino-1,8-naphthyridine) vanadyl(V) chloride |
| 19 tris(2,4-dimethyl-7-amino-1,8-naphthyridine) chromium(III) chloride |
| 20 dichlorobis(2,4-dimethyl-7-amino-1,8-naphthyridine) manganese(II) |
| 21 dichlorobis(2,4-dimethyl-7-amino-1,8-naphthyridine) iron(III) chloride |
| 22 dichloro(2,4-dimethyl-7-amino-1,8-naphthyridine) zinc(II) |

EXAMPLE 23

Preparation of 2-hydroxy-4-methyl-7-amino-1,8-naphthyridine 50 g. of 2,6-diaminopyridine were added to 56 g. (54.6 ml.) of ethyl acetoacetate then 10 ml. of concentrated hydrochloric acid added to the mixture. The solution was heated at 80° C. for 1 hour then cooled and washed with water and ether.

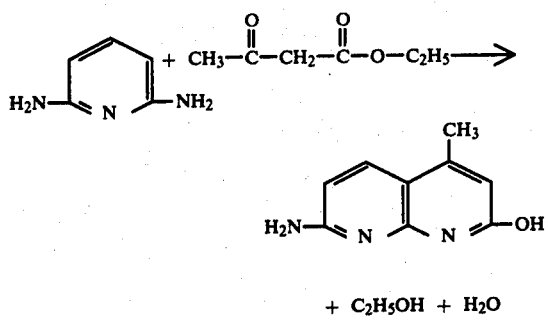

+ $C_2H_5OH$ + $H_2O$ 21.8 grams of 2-hydroxy-4-methyl-7-amino-1,8-naphthyridine was obtained.

EXAMPLE 24

Preparation of a transition metal complex of 2-hydroxy-4-methyl-7-amino-1,8-naphthyridine Into a 500 ml. reaction flask equipped with reflux condenser and mechanical stirrer, were charged 2.37 grams of $CoCl_2.6H_2O$ and 4.92 grams of the naphthyridine compound of Example 23, and 125 ml. of absolute ethanol. This reaction mixture was refluxed for 1 hour. At the end of this period, the reaction mixture was filtered hot and 3.1 grams of product were recovered. The filtrate was cooled to room temperature and filtered again. An additional 1.1 grams of product was recovered.

The product was then recrystallized from water. The melting point was 262°–264° C. The structural formula is given below:

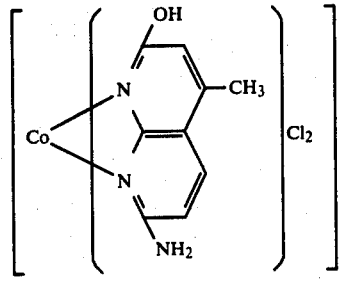

The IUPAC name of this compound is dichloro(2-hydroxy-4-methyl-7-amino-1,8-naphthyridine)cobalt (II).

EXAMPLE 25

Preparation of cobalt iodide complex of 2,4-dimethyl-7-amino-1,8-naphthyridine

The complex was prepared by dissolving 3.1 grams (0.01 m) of $CoI_2$ in 100 ml. of ethanol, dissolving 5.1 grams (0.03 m.) of 2,4-dimethyl-7-amino-1,8-naphthyridine in a separate 100 ml. of ethanol, mixing the solutions and refluxing for 15 minutes. The resulting precipitate was filtered and dried under vacuum at 80° C., with 6.2 grams of blue-violet product resulting. The analysis was as follows: 41.9% C; 4.2% H; and 15.5% N.

This data indicates that the product has the formula:

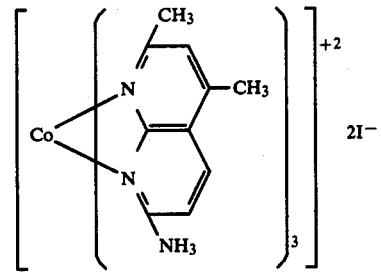

The IUPAC name of this compound is tris(2,4-dimethyl-7-amino-1,8-naphthyridine)cobalt (II) iodide, The new coordination compounds of the invention have various uses. For instance, all of the transition metal compounds of the invention are either white or colored and can be used as a pigment in oil based paint in normal paint-making processes. For instance, the following paint formula can be used.

| Ingredient: | Lbs. |
|---|---|
| Coordination compound of the invention | 300 |
| Zinc oxide | 25 |
| Long-oil soya alkyd resin (60% nonvolatile) | 480 |
| Mineral spirits | 181 |
| Cobalt naphthenate (6% Co) | 3 |
| Lead napthenate (24% Pb) | 3 |
| Calcium naphthenate (4% Ca) | 2 |
| Total | 994 |

Many of the coordination compounds are also useful catalysts, in conjunction with organometallic cocatalysts, to polymerize vinyl chloride. For instance, vinyl chloride can be polymerized at 55° C. using 300 ml. of normal heptane as a solvent with the vinyl chloride being fed from the vapor phase at 20 psig to the reaction vessel which contains a mixture of 0.5 grams of the catalyst and 1 ml. of the cocatalyst, using a polymerization time of two hours, for instance. A suitable cocatalyst for the coordination compounds of Examples 10 and 11 is diethylaluminum chloride, while a suitable cocatalyst for the coordination compounds of Examples 12, 19, 20 and 21 is triisobutylboron. In each case solid polyvinyl chloride is obtained. Similarly, 1,3-butadiene can be polymerized to surprisingly high proportions of 1:4 configuration, over 90 weight percent, using 0.2 grams of the coordination compounds of Examples 4, 15 or 25, together with 2 ml. of diethylaluminum chloride in 500 ml. of benzene at 55° C. The same very high proportion, over 90 weight percent, of solid poly-1,3-butadiene of 1:4 configuration can be obtained when using under the same conditions the cocatalyst combination of 0.2 grams of the coordination compound of Example 10 with 2 ml. of methylaluminumsesquichloride or when using 0.2 grams of the coordination compound of Example 14 together with 4 ml. of methylaluminumsesquichloride. The polymerizations with the catalysts of Examples 10 and 14, together with the respective cocatalysts indicated, gave very surprisingly high productivities, namely, 12,600 and 6,900 grams of polybutadiene per gram of catalyst per hour. These catalysts are so surprisingly active as to give such high yields that the catalyst left in the polymer would not have to be removed therefrom since it is present in such small amounts as not to be harmful. Moreover, the polybutadienes made in the instances set forth with the catalyst combinations using the coordination compounds of Examples 4, 10, 14, 15 and 25 were not only well over 90 percent 1:4 configuration but were also at least 85 percent Cis 1:4 configuration. The polybutadienes produced are useful in the making of automobile tires, while the polyvinyl chlorides made are useful for making shapes such as bottles by conventional blow molding means.

Methods of identifying the compounds of the present invention, including a detailed discussion of the conductance measurements, are disclosed more fully in a thesis by the present inventor which is available in the University of Toledo library, Toledo, Ohio, and is entitled "Coordination Complexes of 2-Methyl-5-Hydroxy-1,8-Naphthyridine".

In summary, there has been provided a process for making the new transition metal salt-substituted 1,8-naphthyridine coordination complex compounds which comprises heating these reactants while dissolved in a non-aqueous mutual solvent for these starting materials until the coordination complex has been formed. There is also provided by this invention a new family of transition metal substituted naphthyridine complex compounds.

As will be evident to those skilled in the art, modifications of this invention can be made or followed in the light of the foregoing disclosure without departing from the spirit and scope of the disclosure or from the scope of the claims.

I claim:
1. A coordination complex compound having the structural formula

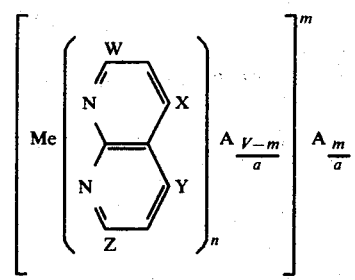

wherein
Me is a transition metal having an atomic number of 21 to 30;
W, X, Y and Z are groups selected from H and electron donating groups lower alkyl, lower alkoxy, (i.e. alkyls and alkoxys having from 1–8 carbon atoms), —OH and —NH$_2$, wherein no more than three H groups are selected;
n is an integer 1, 2 or 3;
A is a nitrate, sulfate or halide;
V is the primary valence of Me;
m is the charge of the coordinated species;
a is the valence of the Anion A;
Me is coordinately bonded with each substituted 1,8-naphthyridine moiety shown in the structural formula solely through one or both ring nitrogen atoms thereof; and when only one such nitrogen atom of each such 1,8-naphthyridine moiety is bonded to Me, n is 2; and
each A within the brackets is coordinately bonded with Me.

2. A coordination complex compound having the structural formula

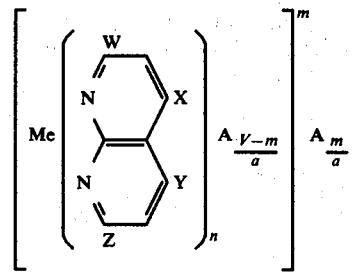

wherein
Me is a transition metal having an aromatic number of 21 to 30;
W, X, Y and Z are groups selected from H and electron donating groups lower alkyl, lower alkoxy, (i.e. alkyls and alkoxys having from 1–8 carbon atoms), —OH and —NH$_2$, wherein no more than two H groups are selected;
n is an integer 1, 2 or 3;
A is a nitrate, sulfate or halide;
V is the primary valence of Me;
m is the charge of the coordinated species;
a is the valence of the Anion A;
Me is coordinately bonded with each substituted 1,8-naphthyridine moiety shown in the structural formula solely through one or both ring nitrogen atoms thereof; and when only one such nitrogen atom of each such 1,8-naphthyridine moiety is bonded to Me, n is 2; and each A within the brackets is coordinately bonded with Me.

3. A coordination complex compound of claim 2 wherein said 1,8-naphthyridine moiety is selected from the group consisting of 2-methyl-7-hydroxy-1,8-naphthyridine; 2-methyl-5-amino-1,8-naphthyridine; 2-methyl-5,7-dihydroxy-1,8-naphthyridine; 2-amino-5,7-dihydroxy-1,8-naphthyridine; 2-methyl-7-amino-1,8-naphthyridine; 2,4-dihydroxy-1,8-naphthyridine; 7-amino-4-hydroxy-1,8-naphthyridine; 2-methyl-5-hydroxy-1,8-naphthyridine; 2,4-dimethyl-7-amino-1,8-naphthyridine; and 2-hydroxy-4-methyl-7-amino-1,8-naphthyridine.

4. Tris(2-methyl-5-hydroxy-1,8-naphthyridine)chromium (III) chloride.

5. Dichlorobis(2-methyl-5-hydroxy-1,8-naphthyridine)chromium (III) chloride.

6. Dichloro(2-methyl-5-hydroxy-1,8-naphthyridine)copper (II).

7. Dichlorobis(2-methyl-5-hydroxy-1,8-naphthyridine)zinc (II).

8. Tris(2-methyl-5-hydroxy-1,8-naphthyridine)cobalt (II) nitrate.

9. Bis(2,4-dimethyl-7-amino-1,8-naphthyridine)cobalt (II) chloride.

10. Bis(2,4-dimethyl-7-amino-1,8-naphthyridine)nickel (II) chloride.

11. Bis(2,4-dimethyl-7-amino-1,8-naphthyridine)copper (II) chloride.

12. Bis(2,4-dimethyl-7-amino-1,8-naphthyridine)cobalt (II) bromide.

13. Dichlorobis(2-,4-dimethyl-7-amino-1,8-naphthyridine)titanium (IV) chloride.

14. Dichloro(2,4-dimethyl-7-amino-1,8-naphthyridine)vanadium (III) chloride.

15. Tris(2,4-dimethyl-7-amino-1,8-naphthyridine)vanadyl (V) chloride.

16. Tris(2,4-dimethyl-7-amino-1,8-naphthyridine)chromium (III) chloride.

17. Dichlorobis(2,4-dimethyl-7-amino-1,8-naphthyridine)manganese (II).

18. Dichlorobis(2,4-dimethyl-7-amino-1,8-naphthyridine)iron (III) chloride.

19. Dichloro(2,4-dimethyl-7-amino-1,8-naphthyridine)zinc (II).

20. Dichloro(2-hydroxy-4-methyl-7-amino-1,8-naphthyridine)cobalt (II).

21. Tris(2,4-dimethyl-7-amino-1,8-naphthyridine)cobalt (II) iodide.

* * * * *

UNITED STATES PATENT AND TRADEMARK OFFICE
CERTIFICATE OF CORRECTION

PATENT NO. : 4,169,092

DATED : September 25, 1979

INVENTOR(S) : John William Bayer

It is certified that error appears in the above—identified patent and that said Letters Patent is hereby corrected as shown below:

On the Title Page insert:

[73] Assignee: Owens-Illinois, Inc.

Signed and Sealed this

Fifteenth Day of April 1980

[SEAL]

Attest:

Attesting Officer

SIDNEY A. DIAMOND

Commissioner of Patents and Trademarks

UNITED STATES PATENT AND TRADEMARK OFFICE
CERTIFICATE OF CORRECTION

PATENT NO. : 4,169,092
DATED : September 25, 1979
INVENTOR(S) : John W. Bayer

It is certified that error appears in the above-identified patent and that said Letters Patent are hereby corrected as shown below:

Col. 7, line 38, the first item in the column headed "Theoretical Compound" should read:

$$CrCl_3 \cdot 2C_9H_8N_2O$$

Col. 9, line 56, the figure in the column headed "%N" should read:

$$10.66$$

Col. 10, the last structure, beginning on line 50, delete "Fe" in the center of the structure and insert --Co--

Col. 12, line 56, before the table, insert the following heading:

--Elemental analysis of recrystallized complexes--

Col. 15, table of solubilities beginning at approximately line 10, the first item in the column headed "Example" should read:

$$2 \ (Cr^{+3})$$

Signed and Sealed this

*Tenth* Day of *June 1980*

[SEAL]

*Attest:*

SIDNEY A. DIAMOND

*Attesting Officer*  *Commissioner of Patents and Trademarks*